(12) United States Patent
Knoer et al.

(10) Patent No.: US 10,662,292 B2
(45) Date of Patent: *May 26, 2020

(54) PROCESS FOR PRODUCING SPHERICAL POLYSILSESQUIOXANE PARTICLES

(71) Applicant: Wacker Chemie AG, Munich (DE)

(72) Inventors: Sebastian Knoer, Emmerting (DE); Kathrin Seilinger, Burghausen (DE)

(73) Assignee: WACKER CHEMIE AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/066,129

(22) PCT Filed: Sep. 27, 2016

(86) PCT No.: PCT/EP2016/072998
§ 371 (c)(1),
(2) Date: Jun. 26, 2018

(87) PCT Pub. No.: WO2018/059670
PCT Pub. Date: Apr. 5, 2018

(65) Prior Publication Data
US 2019/0202992 A1    Jul. 4, 2019

(51) Int. Cl.
| | | |
|---|---|---|
| C08G 77/06 | (2006.01) |
| C08G 77/18 | (2006.01) |
| C08G 77/04 | (2006.01) |
| C08G 77/08 | (2006.01) |
| A61K 8/891 | (2006.01) |
| A61Q 19/00 | (2006.01) |
| A61K 8/02 | (2006.01) |

(52) U.S. Cl.
CPC .............. *C08G 77/06* (2013.01); *A61K 8/025* (2013.01); *A61K 8/891* (2013.01); *A61Q 19/00* (2013.01); *C08G 77/045* (2013.01); *C08G 77/08* (2013.01); *C08G 77/18* (2013.01); *A61K 2800/10* (2013.01)

(58) Field of Classification Search
None
See application file for complete search history.

(56) References Cited

U.S. PATENT DOCUMENTS

| | | | | |
|---|---|---|---|---|
| 4,113,665 A * | 9/1978 | Law | ............... | C08G 77/06 524/779 |
| 4,373,060 A * | 2/1983 | Ching | ............... | C08G 77/26 106/287.12 |
| 4,935,484 A * | 6/1990 | Wolfgruber | ............... | C08G 77/06 528/34 |
| 6,376,078 B1 * | 4/2002 | Inokuchi | ............... | C08J 3/12 427/212 |
| 7,897,714 B2 | 3/2011 | Lee et al. | | |
| 2004/0143081 A1 * | 7/2004 | Oikawa | ............... | C07F 7/21 528/10 |
| 2007/0092821 A1 * | 4/2007 | Sato | ............... | G03G 9/0806 430/108.4 |
| 2007/0249854 A1 * | 10/2007 | Kim | ............... | A61K 8/02 556/419 |
| 2008/0004359 A1 * | 1/2008 | Ma | ............... | C08J 3/09 516/104 |
| 2008/0008944 A1 * | 1/2008 | Sato | ............... | G03G 9/0819 430/48 |
| 2008/0226998 A1 * | 9/2008 | Ishii | ............... | G03G 9/0804 430/48 |
| 2010/0222503 A1 * | 9/2010 | Laine | ............... | C08G 77/045 524/588 |
| 2014/0069488 A1 * | 3/2014 | Tanaka | ............... | G06F 3/045 136/252 |
| 2015/0013763 A1 * | 1/2015 | Matsumura | ............... | H01B 1/22 136/256 |
| 2015/0013764 A1 * | 1/2015 | Matsumura | ............... | H01B 1/22 136/256 |
| 2017/0253781 A1 * | 9/2017 | Kashio | ............... | C08K 3/00 |
| 2017/0267904 A1 * | 9/2017 | Nakayama | ............... | C08K 3/00 |
| 2019/0202992 A1 * | 7/2019 | Knoer | ............... | A61K 8/025 |

FOREIGN PATENT DOCUMENTS

| | | | |
|---|---|---|---|
| CN | 104744700 A | | 7/2015 |
| JP | 4088023 A2 | | 3/1992 |
| JP | 6060239 B2 | | 8/1994 |
| JP | 6248081 A2 | | 9/1994 |
| JP | 10045914 A2 | | 2/1998 |
| JP | 2000186148 A2 | | 7/2000 |
| JP | 2001354770 A | * | 12/2001 |
| JP | 2003183396 A | | 7/2003 |
| JP | 2003335860 A2 | | 11/2003 |
| JP | 3740449 B2 | | 2/2006 |

OTHER PUBLICATIONS

Database WPI Week 200055 Thomson Scientific, London, GB; AN 2000-581615 XP002763905.
Database WPI Week 200422 Thomson Scientific, London, GB; AN 2004-230738 XP002763904.
Database WPI Week 199817 Thomson Scientific, London, GB; AN 1998-189384 XP002763903.
Related U.S. Appl. No. 16/068,007, filed Jul. 3, 2018.

* cited by examiner

*Primary Examiner* — Peter A Salamon
(74) *Attorney, Agent, or Firm* — Brooks Kushman P.C.

(57) ABSTRACT

Spherical polysilsesquioxane particles are prepared by reacting trialkoxysilanes of formula, (I)

$$RSi(OR^1)_3 \qquad (I),$$

where
R represents a $C_{1-16}$ hydrocarbon radical whose carbon chain may be interrupted by nonadjacent —O— groups,
$R^1$ represents a $C_{1-4}$ alkyl radical,
with acidified water having a pH≤6 with stirring to produce a hydrolysate, in a second step mixing the hydrolysate with a solution of NaOH and/or KOH,
and in a third step storing the mixture is stored for at least 8 h before isolating polysilsesquioxane particles thus formed.

19 Claims, No Drawings

PROCESS FOR PRODUCING SPHERICAL POLYSILSESQUIOXANE PARTICLES

CROSS REFERENCE TO RELATED APPLICATIONS

This application is the U.S. National Phase of PCT Appln. No. PCT/EP2016/072998 filed Sep. 27, 2016, the disclosure of which is incorporated in its entirety by reference herein.

BACKGROUND OF THE INVENTION

1. Field of the Invention

The invention relates to a process for producing polysilsesquioxane particles by hydrolysis of trialkoxysilane and condensation of the hydrolysate.

2. Description of the Related Art

The prior art, for example JP3970449B2, JPH06248081A and JPH0488023A, discloses various processes for generating spherical polymethylsilsesquioxane particles. JP3970449B2 describes optimization of the space-time yield and control of the particle size. No process has hitherto been described which allows control of the agglomerization behavior of the particles.

SUMMARY OF THE INVENTION

The present invention provides a process for producing spherical polysilsesquioxane particles in which in a first step trialkoxysilane(s) of general formula, (I)

    (I), in which
R represents a hydrocarbon radical having 1 to 16 carbon atoms whose carbon chain may be interrupted by nonadjacent —O— groups,
$R^1$ represents a $C_1$- to $C_4$-alkyl radical,
is reacted with acidified water having a pH of not more than 6 with stirring to afford a hydrolysate, in a second step the hydrolysate is mixed with a solution of alkali metal hydroxide selected from NaOH and KOH or a mixture thereof and in a third step the mixture is stored for at least 8 h before the polysilsesquioxane particles are isolated.

DETAILED DESCRIPTION OF THE PREFERRED EMBODIMENT

It was found that through the use of a solution of an alkali metal hydroxide selected from NaOH and KOH in combination with the above-described process parameters, very largely agglomerization-free spherical polysilsesquioxane particles may be obtained. Grinding of the particles is not necessary. Such particles exhibit highly advantageous behavior, in particular for cosmetic applications. They are converted into a liquid-like flowable state (fluidization) even at low shear and are therefore exceptionally easy to spread and provide a velvety skin feel. This behavior is not observable for agglomerated particles. These undergo balling upon spreading on the skin.

Fluid, i.e. liquid-like behavior, is apparent in particular immediately after shaking of the polysilsesquioxane particles. The greater the volume increase, the more pronounced the fluid behavior. A material which exhibits a 50% volume increase already shows fluid behavior which for example manifests in that the material in the container—immediately after shaking—flows to and fro similarly to a liquid upon tilting of the container. A material with a 50% volume increase undergoes very rapid sedimentation and returns into the non-fluid initial stage which is disadvantageous. The spherical polysilsesquioxane particles preferably show at least a 100% volume increase.

The dried unground polysilsesquioxane particles preferably comprise at least 30% by weight, more preferably at least 40% by weight, and most preferably at least 50% by weight of a sieve fraction <20 µm.

The dried unground polysilsesquioxane particles preferably comprise at least 60% by weight, more preferably at least 70% by weight, of a sieve fraction <40 µm.

The dried unground polysilsesquioxane particles preferably comprise less than 25% by weight, more preferably less than 20% by weight, and most preferably less than 15% by weight, of a sieve fraction >100 µm.

R preferably represents an alkyl radical having 1 to 6 carbon atoms or phenyl radical, in particular ethyl or methyl radicals.

$R^1$ preferably represents a methyl, ethyl or n-propyl radical, in particular a methyl radical.

Preferred trialkoxysilanes of general formula (I) are methyltrimethoxysilane, methyltriethoxysilane, methyltri-n-propoxysilane, methyltriisopropoxysilane and methyltris(2-methoxyethoxy)silane and mixtures thereof.

The reaction to afford a hydrolysate is preferably effected in acidified water having a pH of not more than 5.5, more preferably not more than 4.5 and preferably at least 1, more preferably at least 2, and in particular at least 2.3.

The water employed is preferably demineralized, and before acidification preferably has a conductivity of not more than 50 µS/cm, more preferably not more than 30 µS/cm, yet more preferably not more than 20 µS/cm, and most preferably not more than 10 µS/cm, in each case measured at 20° C.

The water employed may be acidified using Brønsted acids or Lewis acids.

Examples of Lewis acids are $BF_3$, $AlCl_3$, $TiCl_3$, $SnCl_4$, $SO_3$, $PCl_5$, $POCl_3$, $FeCl_3$ and hydrates thereof, and $ZnCl_2$. Examples of Brønsted acids are hydrochloric acid, hydrobromic acid, sulfuric acid, nitric acid, nitrous acid, chlorosulfonic acid, phosphoric, such as ortho-, meta- and polyphosphoric acids, boric acids, selenous acid, nitric acid, carboxylic acids, such as formic acid, acetic acid, propionic acid, citric acid and oxalic acid, haloacetic acids, such as trichloroacetic and trifluoroacetic acid, p-toluene sulfonic acid, acidic ion exchangers, acidic zeolites and acid-activated Fuller's earth.

Hydrochloric acid, hydrobromic acid and acetic acid are preferred.

The acidification of the water may be effected before the conversion to the hydrolysate, simultaneously with the conversion or both before the conversion and simultaneously with the conversion. In one particular embodiment the water is partly acidified with hydrochloric acid before the reaction to afford a hydrolysate and a further portion of hydrochloric acid is introduced through the trialkoxysilanes of general formula (I).

Hydrolysis of the trialkoxysilane is a weakly exothermic reaction. In a preferred embodiment the temperature in the first step is maintained, optionally by heating or cooling, at 0° C. to 60° C., more preferably at 10° C. to 50° C., yet more preferably at 15° C. to 40° C., still more preferably at 15° C. to 30° C., and in particular at 15-25° C., wherein the temperature variation after attainment of the target temperature is by preference less than 10° C., more preferably less than 5° C. The metered addition of the trialkoxysilane may be commenced before or after attainment of the target temperature as desired.

In another embodiment the trialkoxysilane is metered in in one portion. The heat is not actively or only partly removed by cooling. In this embodiment an exothermic increase in temperature takes place after addition of the trialkoxysilane. The temperature of the reaction in the first step is 20° C. to 80° C., preferably up to 60° C.

Preferably, the trialkoxysilane is metered in over 0.5 to 5 h, more preferably to not more than 2 h. Between rapid addition and metered addition there is a fluid transition of inventive embodiments, i.e. it is possible for example to effect addition rapidly in 15 min with partial removal of heat up to not more than 40° C. or it is possible to effect metered addition over 2 h but only perform a low level of cooling thus initially allowing a temperature increase to 30° C. and maintaining at this temperature.

Metered addition at a constant temperature is particularly preferred.

It is preferable when, in the first step, 5 to 43 parts by weight, preferably 11 to 34 parts by weight, and in particular 13 to 25 parts by weight, of trialkoxysilane are added per 100 parts by weight of water.

The commixing in the first step may be effected by means of a static mixer or preferably by means of a stirrer.

It is preferable when, after metered addition of the trialkoxysilane, the mixture is subjected to further stirring for 5 min to 5 h, more preferably 10 min to 3 h, and in particular 15 min to 1.5 h. The further stirring time is preferably chosen such that the sum of the addition time for the silane and the further stirring time do not exceed 6 h.

The temperature during the further stirring is maintained at 0° C. to 60° C., preferably at 10° C. to 50° C., more preferably at 10° C. to 40° C., yet more preferably at 10° C. to 30° C., and in particular at 15° C. to 25° C. It is preferable when the difference in the temperature of the reaction in the first step and the temperature during the further stirring is less than 20° C., more preferably less than 10° C., and in particular less than 5° C.

It is preferable when, in the second step, a solution of alkali metal hydroxide in water or in an alkanol having 1 to 3 carbon atoms is employed. Preferred alkanols are 1-propanol, 2-propanol, ethanol and in particular methanol. A solution of alkali metal hydroxide in water is likewise preferred. Diluted or concentrated solutions of alkali metal hydroxide of 0.001 to 1100 g/l at 20° C., preferably 0.01 to 500 g/l, and more preferably 0.1 to 500 g/l, are suitable.

When using a solution of alkali metal hydroxide in an alkanol, the particles exhibit reduced adhesion to one another, show a reduced degree of agglomeration, and have a lower propensity for clumping. The particles show a dryer skin feel preferred in cosmetic applications.

KOH is preferred as the alkali metal hydroxide.

Also possible as an alternative to NaOH and KOH is the use of an NaOH- or KOH-former which in the second step immediately reacts with the water present in the hydrolysate to afford NaOH or KOH. Examples thereof are sodium ethoxide, potassium methoxide, NaH and KH. In this embodiment the use of sodium ethoxide or potassium methoxide in methanolic solution is preferred.

It is preferable when sufficient solution of alkali metal hydroxide is added to ensure that a pH of at least 6, preferably at least 6.5 and not more than 10, preferably not more than 9.5 is achieved in each case immediately after addition of alkali metal hydroxide. Particle size may be influenced by the addition of the amount of alkali metal hydroxide, wherein lower pHs result in larger particles. The especially preferred pH is 7.5 to 9.

The solution of alkali metal hydroxide is preferably added over 10 seconds to 10 minutes, in particular over 1 to 3 minutes, preferably with vigorous and short stirring.

In a preferred embodiment the temperature of the addition of alkali metal hydroxide in the second step is maintained at 0° C. to 60° C., more preferably at 10° C. to 50° C., yet more preferably at 10° C. to 40° C., still more preferably at 10° C. to 30° C., and in particular at 15° C. to 25° C. It is preferable when the difference in the temperature during further stirring and the temperature of addition of alkali metal hydroxide is less than 20° C., more preferably less than 10° C., and in particular less than 5° C.

The commixing in the second step may be effected by means of a static mixer or preferably by means of a stirrer.

After the second step the commixing is preferably terminated within 10 minutes, preferably within 5 minutes. After the second step the mixture is not moved, by preference, for at least 1 h, more preferably at least 1.5 h, and most preferably at least 2.5 h. A stirrer may subsequently be switched on at a low speed to prevent sedimentation of the particles. This is optional and not necessary since the sedimented polysilsesquioxane particles may be stirred up readily.

After the second step the temperature of the mixture is preferably altered by not more than 20° C., more preferably not more than 10° C., for at least 1 h, preferably at least 1.5 h, and more preferably at least 2.5 h.

If in the starting phase in the third step in which the formation of the particles is effected the mixture is moved this results in an increased incidence of malformed, coalesced or agglomerated particles.

In a preferred embodiment in the third step the mixture is not moved until isolation of the polysilsesquioxane particles.

It is preferable when in the third step the mixture is stored for at least 12 h, more preferably at least 14 h, and in particular at least 18 h, before the polysilsesquioxane particles are isolated. Storage times of up to 12 weeks are also possible.

A clouding is usually visible even after 1-30 minutes.

The temperature in the third step is by preference 0° C. to 60° C., more preferably 10° C. to 50° C., yet more preferably 10° C. to 40° C., still more preferably 10° C. to 30° C., and in particular 15° C. to 25° C. Lower temperatures form larger particles and higher temperatures form smaller particles.

At a temperature of 15° C. to 25° C. there is little if any temperature gradient in the reaction mixture toward the outer region, thus a minimal thermal gradient between the reactor wall and the reaction solution and thus minimized thermal convection during the precipitation of the particles.

The process according to the invention may be run as a batch, semi-batch or continuous process.

After the third step the particles are preferably isolated, preferably by filtration or centrifugation. After isolation the particles are preferably washed with DM water or alcohol and preferably dried.

Drying is preferably effected at 40° C. to 250° C., more preferably at 100° C. to 240° C., and most preferably at 140° C. to 220° C.

Drying may be effected at atmospheric pressure or at reduced pressure. During drying a condensation of Si—OH groups also takes place which according to kinetics measurements takes place preferably above 150° C., more advantageously above 180° C., ideally above 200° C. While particles which have been dried at 100° C. for a long time are dry they also have a high Si—OH content. At 150° C. the Si—OH content is markedly reduced but not yet fully removed, at 200° C. Si—OH groups are again significantly reduced. A reduced Si—OH content results in advantages in the spreading behavior and in the fluidization of the particles.

The particles are preferably dried for 0.5 to 100 h, more preferably 0.5 to 24 h, and in particular 1 to 14 h.

A particularly high freedom from agglomeration of the polysilsesquioxane particles may be achieved by means of a subsequent milling.

The polysilsesquioxane particles preferably exhibit a spherical shape upon examination in an electron microscope. The spherical polysilsesquioxane particles preferably exhibit an average sphericity y of at least 0.6, in particular at least 0.7. The spherical polysilsesquioxane particles preferably have an average roundness x of at least 0.6, in particular at least 0.7. The roundness x and sphericity y may be determined according to DIN EN ISO 13503-2, page 37, annex B.3, in particular FIG. B.1.

It is preferable when all process steps are performed at the pressure of ambient atmosphere, i.e. about 0.1 MPa (abs.); They may also be performed at higher or lower pressures. Preferred are pressures of at least 0.08 MPa (abs.) and more preferably at least 0.09 MPa (abs.), preferably not more than 0.2 MPa (abs.), and in particular not more than 0.15 MPa (abs.).

All of the abovementioned symbols of the abovementioned formulae are defined each independently of one another. The silicon atom is tetravalent in all formulae.

In the examples which follow, unless otherwise stated, in each case all amounts and percentages are based on weight, all pressures are 0.10 MPa (abs.) and all temperatures are 20° C.

EXAMPLES

Volume-Weighted Particle Size Distribution $d_{50}$

Determination of the volume-weighted particle size distribution is by means of static laser diffraction with a Sympatec HELOS instrument fitted with a RODOS dry disperser with 2 bar of compressed air as the dispersion medium. The $d_{50}$ indicates the median particle size.

Sieve Analysis:

Sieve analysis was by means of dry sieving using an analytical Retsch AS 200 basic sieve machine at 100% amplitude. For analysis four sieves according to DIN ISO 3310 having the following mesh sizes were stacked: 200 µm, 100 µm, 40 µm, 20 µm, bottom. In each case 50 g of substance was applied atop the first sieve (200 µm) and sieved for 10 minutes.

Determination of Fluidization and Volume Increase:

6.0 g of polysilsesquioxane particles are introduced into a 50 ml PP centrifuge tube, shaken vigorously for 30 seconds and left to stand for 1 h on a level plane. If required a level surface is subsequently generated by tapping. The (settled) volume of the sample is read off. The container is sealed and shaken vigorously for at least 30 seconds until all of the material is dispersed. The centrifuge tube is placed straight back on the plane and the (shaken) volume read off immediately thereafter. Shaking and reading off is repeated a total of three times and from the determined values the average volume (shaken, average of three experiments) determined. The volume increase is then calculated with the following formula:

Volume increase=volume(shaken,average of three experiments)×100/volume(settled)

The microscopic examinations were performed with a Zeiss SUPRA 55 VP scanning electron microscope. Prior to examination the samples were sputtered with gold to prevent charging phenomena using a Safematic CCU-010 sputter coater.

The spherical polysilsesquioxane particles of examples 1 to 3 have an average sphericity y of 0.8 and an average roundness x of 0.85 according to DIN EN ISO 13503-2, page 37, annex B.3, FIGURE B.1.

Example 1

1328 g of demineralized water having a conductivity of 0.1 µS/cm is initially charged into a glass flask and temperature-controlled to 20° C. The flask contents are stirred at 300 rpm. The pH is adjusted to a value of 4.40 by addition of 0.1 molar hydrochloric acid. 291.6 g of methyltrimethoxysilane are metered in over 1 h and the temperature is maintained at 20° C. After termination of the metered addition the flask contents are stirred at 20° C. for 1 h. 65.49 g of 0.1 molar aqueous KOH solution are added over 1 min at 20° C. and mixed for a total of 3 min to form a homogeneous mixture. The stirrer is then switched off. After 21 h the precipitated particles are filtered off, washed with DM water and dried in a drying cabinet at 150° C. for 18 hours.

Example 2

The example was performed according to the process of example 1, except that 65.84 g of 0.1 molar aqueous NaOH solution were added to achieve precipitation.

Example 3

The example was performed according to the process of example 1, except that 65.49 g of 0.1 molar methanolic KOH solution were added to achieve precipitation.

Comparative Example C1, (Noninventive)

The example was performed according to the process of example 1. The same base was used to achieve precipitation but the precipitated particles were filtered off after a hold time of only 4 h after base addition, washed with DM water and dried in a drying cabinet at 150° C. for 18 hours.

Comparative Example C2, (Noninventive)

The example was performed according to the process of example 2. The same base was used to achieve precipitation but the precipitated particles were filtered off after a hold time of only 4 h after base addition, washed with DM water and dried in a drying cabinet at 150° C. for 18 hours.

Comparative Example C3, (Noninventive)

The example was performed according to the process of example 1 except that 7.96 g of 1 molar aqueous ammonia solution were added to achieve precipitation.

Comparative Example C4, (Noninventive)

The example was performed according to the process of example 3. The same base was used to achieve precipitation but the precipitated particles were filtered off after a hold time of only 4 h after base addition, washed with DM water and dried in a drying cabinet at 150° C. for 18 hours.

Comparative Example C5, (Noninventive)

The example was performed according to the process of example 1 except that 71.73 g of 0.1 molar aqueous diethylamine solution were added to achieve precipitation.

Comparative Example C6, (Noninventive)

The example was performed according to the process of example 1 except that 243.99 g of 0.1 molar aqueous calcium hydroxide solution were added to achieve precipitation.

Comparative Example C7, (Noninventive)

The noninventive particles produced according to comparative example 3 were dispersed with an Alpine 100AFG fluidized bed opposed jet mill at a pressure of 7 bar and a sifter speed of 12,000 rpm.

After spreading, the sensory properties of the respective residue were evaluated.

The residues of the inventive polysilsesquioxane particles from the examples 1 and 3 were each evaluated as preferably silky smooth, wherein example 3 exhibits a comparatively more pronounced dry skin feel which is particularly preferable for cosmetic applications. The residue of the noninventive polysilsesquioxane particles from comparative example C3 was evaluated as unsuitably waxy/chalky.

The invention claimed is:

1. A process for producing spherical polysilsesquioxane particles, comprising:
    a) in a first step, reacting at least one trialkoxysilane of the formula, (I)
    $$RSi(OR^1)_3 \quad (I),$$
    in which
    R represents a hydrocarbon radical having 1 to 16 carbon atoms whose carbon chain is optionally interrupted by nonadjacent —O— groups, and

TABLE 1

| | | Example | | | | | | | | | |
|---|---|---|---|---|---|---|---|---|---|---|---|
| | | 1 | 2 | 3 | C1* | C2* | C3* | C4* | C5* | C6* | C7* |
| Precipitation base | | KOH | NaOH | KOH (MeOH) | KOH | NaOH | Ammonia | Ammonia | Diethylamine | Ca(OH)2 | Ammonia |
| Precipitation time** | hrs. | 21 | 21 | 21 | 4 | 4 | 21 | 4 | 21 | 21 | 21 |
| Milling | | no | no | no | no | no | no | no | no | no | yes |
| Sieve fraction | <20 μm | 68 | 59 | 67 | 0 | 0 | 1 | 0 | 4 | 25 | 35 |
| Sieve fraction | 20-40 μm | 10 | 14 | 17 | 0 | 0 | 16 | 0 | 55 | 19 | 55 |
| Sieve fraction | 40-100 μm | 10 | 14 | 9 | 8 | 5 | 41 | 7 | 16 | 18 | 5 |
| Sieve fraction | 100-200 μm | 7 | 6 | 5 | 33 | 32 | 27 | 31 | 13 | 20 | 3 |
| Sieve fraction | >200 μm | 5 | 7 | 3 | 58 | 62 | 15 | 62 | 12 | 18 | 2 |
| Sum of fractions < 40 μm | | 78 | 73 | 84 | 0 | 0 | 17 | 0 | 59 | 44 | 90 |
| Sum of fractions > 100 μm | | 12 | 13 | 8 | 91 | 94 | 68 | 93 | 25 | 37 | 5 |
| Median particle diameter $d_{50}$ | μm | 4.10 | 4.05 | 4.45 | 3.94 | 4.04 | 4.22 | 5.29 | 5.30 | 4.14 | 4.22 |
| Fluidization | | yes | yes | yes | no | no | yes | no | yes | yes | yes |
| Volume increase | % | 170 | n.d. | 210 | 0 | 0 | 130 | 0 | n.d. | n.d. | n.d. | n.d. not determined
*noninventive
**hold time in hours after base addition

Example 4: Evaluation of Sensory Properties

Evaluation of the sensory properties of the inventive spherical polysilsesquioxane particles from examples 1 and 3 and the noninventive polysilsesquioxane particles from the comparative example C3 was performed by a trained panel of five testers. The ease of spreadability of the particles and the propensity for clumping or agglomeration during spreading were evaluated. Evaluation was according to a scale of 0 to 2, wherein 2 denotes best spreadability and lowest agglomeration propensity.

TABLE 2

| Example | Spreadability | Agglomeration propensity |
|---|---|---|
| Example 1 | 1 | 1 |
| Example 3 | 2 | 2 |
| Example C3 | 0 | 0 |

$R^1$ represents a $C_1$- to $C_4$-alkyl radical,
with acidified water having a pH of not more than 6 with stirring to afford a hydrolysate,
    b) in a second step, mixing the hydrolysate with a solution comprising NaOH, KOH, or a mixture thereof, and
    c) in a third step, storing the mixture in the substantial absence of agitation for at least 8 h, forming spherical polysilsesquioxane particles, before isolating the polysilsesquioxane particles.

2. The process of claim 1, in which R is an ethyl radical or methyl radical.

3. The process of claim 1, in which $R^1$ is an ethyl radical or methyl radical.

4. The process of claim 2, in which $R^1$ is an ethyl radical or methyl radical.

5. The process of claim 1, in which the reaction to afford the hydrolysate in step b) is effected at a pH of 4.5 to 2.

6. The process of claim 4, in which the reaction to afford the hydrolysate in step b) is effected at a pH of 4.5 to 2.

7. The process of claim 1, in which the temperature of the reaction in step a) is 0° C. to 60° C.

8. The process of claim 1, in which in the first step, 5 to 43 parts by weight of trialkoxysilane are added per 100 parts by weight of water.

9. The process of claim 1, in which in the second step a solution of alkali metal hydroxide in water or in an alkanol having 1 to 3 carbon atoms is employed as the solution comprising KOH, NaOH, or a mixture thereof.

10. The process of claim 1, in which sufficient solution of alkali metal hydroxide is added to obtain a pH of 6.5 to 9.5 following addition of alkali metal hydroxide.

11. The process of claim 1, in which the temperature of the addition of alkali metal hydroxide in the second step b) is 10° C. to 40° C.

12. The process of claim 1, in which in the third step c) the mixture is stored for at least 14 h before the polysilsesquioxane particles are isolated.

13. The process of claim 1, in which after the third step c) the particles are isolated by filtration or centrifugation.

14. The process of claim 1, wherein the mixture in step c) is not moved until prior to isolation of the polysilsesquioxane particles.

15. The process of claim 1, wherein the isolated polysilsesquioxane particles have an average sphericity of ≥0.6 as measured in accordance with DIN EN 13503-2, p. 37, annex B.3.

16. The process of claim 1, wherein the isolated polysilsesquioxane particles have an average sphericity of ≥0.7 as measured in accordance with DIN EN 13503-2, p. 37, annex B.3.

17. The process of claim 1, wherein the isolated polysilsesquioxane particles have an average roundness of ≥0.6 as measured in accordance with DIN EN 13503-2, p. 37, annex B.3.

18. The process of claim 1, wherein the isolated polysilsesquioxane particles have an average roundness of ≥0.7 as measured in accordance with DIN EN 13503-2, p. 37, annex B.3.

19. The process of claim 1, wherein the isolated polysilsesquioxane particles are fluidizable into a flowable state.

* * * * *